US009132233B2

(12) United States Patent
Lee

(10) Patent No.: US 9,132,233 B2
(45) Date of Patent: Sep. 15, 2015

(54) INFUSION CONTROL DEVICE

(75) Inventor: Freddie Eng Hwee Lee, Singapore (SG)

(73) Assignee: B. BRAUN MELSUNGEN AG, Melsungen (DE)

( * ) Notice: Subject to any disclaimer, the term of this patent is extended or adjusted under 35 U.S.C. 154(b) by 273 days.

(21) Appl. No.: 12/869,316

(22) Filed: Aug. 26, 2010

(65) Prior Publication Data

US 2012/0053556 A1 Mar. 1, 2012

(51) Int. Cl.
*A61M 5/168* (2006.01)
*A61M 39/28* (2006.01)
*A61M 5/14* (2006.01)
*A61M 39/00* (2006.01)

(52) U.S. Cl.
CPC ............ *A61M 5/16877* (2013.01); *A61M 5/141* (2013.01); *A61M 5/16809* (2013.01); *A61M 39/284* (2013.01); *A61M 2005/1402* (2013.01); *A61M 2005/1403* (2013.01); *A61M 2005/1405* (2013.01); *A61M 2039/0009* (2013.01); *A61M 2205/273* (2013.01)

(58) Field of Classification Search
CPC ............. A61M 2005/1402; A61M 2005/1403; A61M 2005/1405; A61M 5/141; A61M 5/16809; A61M 5/16877
USPC ......... 604/500, 506, 513, 131, 151, 246, 247, 604/248, 249, 250, 256, 257, 258, 533, 534, 604/535, 537, 538, 539, 905
See application file for complete search history.

(56) References Cited

U.S. PATENT DOCUMENTS

| 4,256,104 | A | * | 3/1981 | Muetterties et al. ............ 604/81 |
| 5,011,477 | A | | 4/1991 | Winchell et al. |
| 5,105,983 | A | | 4/1992 | Sancoff et al. |
| 5,304,153 | A | | 4/1994 | Tsujikawa |
| 5,807,312 | A | | 9/1998 | Dzwonkiewicz |
| 5,906,597 | A | | 5/1999 | McPhee |
| 6,283,944 | B1 | | 9/2001 | McMullen |
| 6,702,779 | B2 | * | 3/2004 | Connelly et al. ............ 604/93.01 |
| 6,981,967 | B2 | * | 1/2006 | Massengale et al. ......... 604/174 |
| 7,559,926 | B1 | | 7/2009 | Blischak |
| 7,618,432 | B2 | | 11/2009 | Pedersen et al. |
| 2008/0257412 | A1 | | 10/2008 | Gordon |

FOREIGN PATENT DOCUMENTS

| JP | S56-500007 | 1/1981 |
| JP | 2002-233571 | 8/2002 |
| JP | 2004-506491 | 3/2004 |
| JP | 2004-528137 | 9/2004 |
| WO | WO80/01756 | 9/1980 |

(Continued)

OTHER PUBLICATIONS

International Search Report for PCT/IB2011/001930 mailed Mar. 15, 2012.

(Continued)

*Primary Examiner* — Kevin C Sirmons
*Assistant Examiner* — Shefali Patel
(74) *Attorney, Agent, or Firm* — RatnerPrestia

(57) ABSTRACT

A medical fluid control device includes an actuator that is selectively operable to cause a fluid to be delivered from a fluid source to a patient at a basal rate of flow via a first flow path, or cause a bolus dose of the fluid to be delivered from a bolus reservoir to the patient via a second flow path.

18 Claims, 12 Drawing Sheets

(56) References Cited

FOREIGN PATENT DOCUMENTS

| | | |
|---|---|---|
| WO | WO02/15965 | 2/2002 |
| WO | WO02/098493 | 12/2002 |

OTHER PUBLICATIONS

Office Action for U.S. Appl. No. 12/835,209 mailed Feb. 2, 2012.

European Office Action for EP 11 768 098.3 dated Jun. 13, 2014.

Korean Office Action with translation for Korean Application No. KR 2013-7007550 dated Jul. 23, 2014.

Korean Office Action with translation for Korean Application No. KR 2013-7007550 dated Jan. 26, 2015.

Japanese Office Action, with translation, for JP 2013-525374 dated Jun. 3, 2015.

* cited by examiner

INFUSION CONTROL DEVICE

BACKGROUND

The ability of a patient to self-deliver medication, e.g., in offsite therapy or where a nurse or caregiver is not immediately available, offers a solution to logistical issues arising from medical situations such as chronic therapy. Patient-controlled analgesia (PCA) is widely accepted in the field of pain management, as it enables patients to provide themselves with pain relief at times when such relief is most needed. PCA devices ideally include safeguards against overdoses and are easy and safe for a patient with little or no medical training to operate.

PCA devices often allow additional bolus doses of a predetermined amount of medication to be delivered to the patient, for instance when a patient needs or desires additional pain relief. After the bolus dose is delivered, the patient may continue to receive a normal (basal) rate of continuous infusion from an IV pump to which the PCA device is connected. In some cases, the basal rate is zero, meaning that the patient receives medication only when the PCA device is actuated.

SUMMARY

In general, in one aspect, the invention features a device for controlling the delivery of a fluid from a fluid source to a patient. The device includes a first flow path between the fluid source and the patient, the first flow path for delivering fluid from the fluid source to the patient at a basal rate of flow; a second flow path between the fluid source and the patient, the second flow path including: a bolus reservoir; a bolus valve disposed between the bolus reservoir and the patient; a first branch in which the fluid source is in fluid communication with the bolus reservoir and the bolus valve; and a second branch in which the fluid source is in fluid communication with a branch valve, the bolus reservoir and the bolus valve; and an actuator that is selectively operable to place the device in one of at the following modes: a priming mode in which the bolus valve and the branch valve are open and fluid flows through the first flow path, the first branch of the second flow path, and the second branch of the second flow path; a fill mode in which the bolus valve is closed and the branch valve is open and fluid flows from the fluid source to the bolus reservoir via the second branch of the second flow path; and a standby mode in which the bolus valve and the branch valve are closed and fluid flows between the fluid source and the patient via the first flow path.

Embodiments of the invention may include one or more of the following features.

In the standby mode, the actuator is selectively further operable to open the branch valve and apply pressure to the bolus reservoir to cause fluid stored in the bolus reservoir to flow to the patient. The actuator may be depressed responsive to user action.

The first flow path may include a basal restrictor tube. The basal restrictor tube may be dimensioned to allow fluid flow through the first flow path at the basal rate of flow.

The device may be configured to allow filling of the bolus reservoir while fluid is being delivered to the patient via the first flow path.

The first branch may include a branch restrictor tube dimensioned to allow fluid flow at a bolus filling rate. The bolus filling rate may be preselected based on a desired amount of time needed to fill the bolus reservoir with fluid from the fluid source via the first branch of the second flow path. In the standby mode, fluid may flow between the fluid source and the bolus reservoir via the first branch of the second flow path until the bolus reservoir is filled.

The device may be further configured to operate in a priming mode in which the bolus valve and the branch valve are open and fluid flows between the fluid source and an output of the device via the first flow path and the second flow path.

The actuator may be rotatable to selective rotatable to place the device in one of at least the following modes: the standby mode, the fill mode, and the bolus infusion mode. The actuator may be configured to be depressed to select the bolus infusion mode.

The bolus valve and the branch valve may be pinch tubes.

The actuator may be further configured to open the branch valve to allow fluid flow between the fluid source and the bolus reservoir.

When the actuator is depressed, pressure may be applied to the bolus reservoir such that fluid stored in the bolus reservoir is expelled.

The actuator may be a knob operable by the patient.

The fluid source may be an infusion pump.

In general, in another aspect, the invention features a method for controlling the delivery of fluid from a fluid source to a patient using a device having a first flow path and a second flow path parallel to the first flow path. The method includes providing fluid to the patient via the first flow path at a basal rate of flow; in response to actuation by an actuator, allowing delivery to the patient of fluid stored in a bolus reservoir disposed along the second flow path.

Embodiments of the invention may include one or more of the following features.

The method of allowing delivery of fluid stored in the bolus reservoir may include opening a bolus valve disposed along the second flow path between the bolus reservoir and the patient. The method may further include filling the bolus reservoir with fluid from the fluid source while fluid is being provided to the patient via the first flow path. The method of filling the bolus reservoir may include providing fluid flow from the fluid source to the bolus reservoir via a first branch of the second flow path. The method of filling the bolus reservoir may include providing fluid flow from the fluid source to the bolus reservoir via a second branch of the second flow path. The method of providing fluid flow via the second branch of the second flow path may include opening a branch valve disposed along the second branch.

The infusion control device described herein has a number of advantages. The patient receiving medication can receive continuous infusion of medication and can self-deliver a bolus dose as needed without the danger of an accidental or intentional overdose.

Priming and filling of the bolus reservoir is rapid and efficient. The basal flow rate of fluid or medication to the patient remains constant even when the bolus is being refilled immediately after bolus administration.

The actuator knob has a simple design with a dual function, allowing both quick priming and an initial rapid fill of the bolus in additional to ordinary bolus dose administration.

Other features and advantages of the invention are apparent from the following description and from the claims.

DETAILED DESCRIPTION

Figure 1:
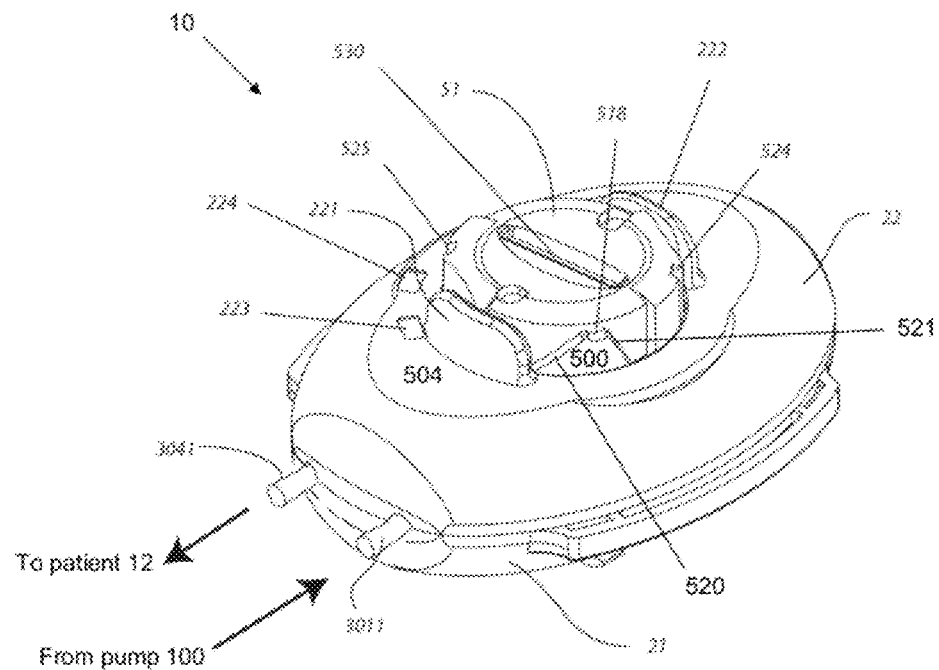
FIG. 1 is a schematic diagram of an infusion control device.

Referring to FIG. 1, an infusion control device 10 is connected to a pump 100, such as an elastomeric pump, via an input tube 3011. Infusion control device 10 is operable by a patient 12 or another person (e.g., a caretaker of the patient) to control fluid delivery (e.g., delivery of medication) to the patient via an output tube 3041. In general, infusion control device 10 allows fluid delivery at a predetermined basal rate of flow. However, at times, the patient may need or desire an additional bolus dose of fluid, e.g., to provide a boost in pain relief. Infusion control device 10 enables the delivery of a bolus dose followed by an immediate return to the basal flow rate. Once the bolus dose has been delivered, the infusion control device also provides for a predetermined "lock-out" period before the next bolus dose can be delivered, preventing accidental or intentional overdose. In some embodiments, infusion control device 10 and pump 100 are provided as a single unit.

Infusion control device 10 is formed of a bottom housing 21 and a top housing 22, within which is disposed an actuator knob 51. Knob 51 is rotatable about a central vertical axis to allow the selection of a particular fluid pathway through the device corresponding to a desired mode of operation (e.g., basal flow rate, bolus administration, or priming and/or filling of the bolus reservoir). Knob 51 is stabilized by guides 221, 222, which help to maintain the position of the knob.

Figure 2A:
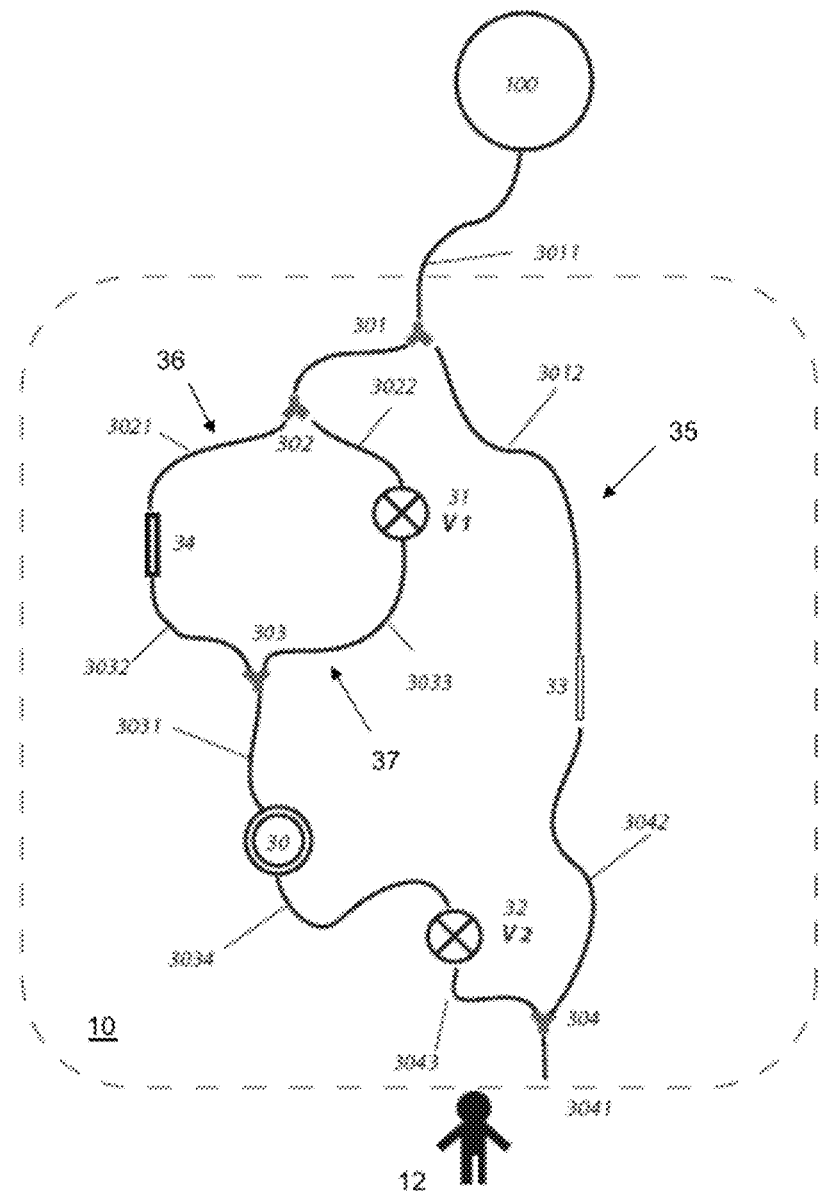
FIG. 2A is a diagram of the fluid flow pathways through the infusion control device.
Figure 2B:
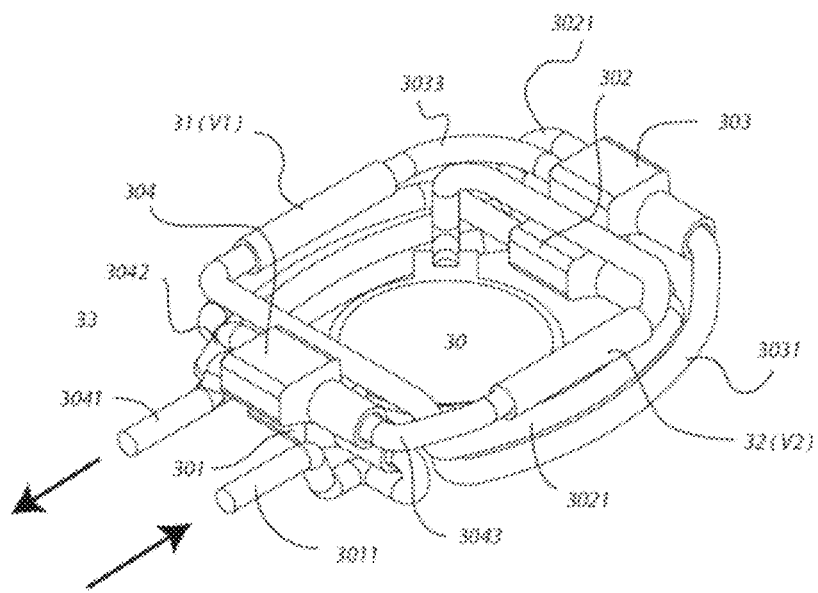
FIG. 2B is a schematic diagram of the fluid flow pathways through the infusion control device.

Referring to FIGS. 2A and 2B, three flow paths are provided through infusion control device 10: a basal flow path 35, a first bolus flow path 36, and a second bolus flow path 37. In basal flow path 35, fluid flows between an input node 301 and an output node 304 via tubing sections 3012 and 3042 and a basal restrictor tube 33. Fluid in first bolus flow path 36 flows between a first branching node 302 and a second branching node 303 via tubing sections 3021 and 3032 and a bolus restrictor tube 34. In second bolus flow path 37, fluid flows between branching nodes 302 and 304 via tubing sections 3022 and 3033 and a valve 31. At second branching node 303, the first and second bolus flow paths 36, 37 combine and flow through a tubing section 3031 into a bolus reservoir 30. From the bolus reservoir, fluid exits to output node 304 via tubing sections 3034 and 3043 and a valve 32.

To prime infusion control device 10 prior to its initial use, knob 51 is rotated to a position at which valves 31 and 32 are both opened, allowing fluid to flow through all three available flow paths 35, 36, and 37. During priming, both restrictor tubes 33 and 34 and bolus reservoir 30 are inundated with fluid, allowing priming to take place rapidly. In particular, the opening of valve 31 provides a low-resistance pathway between pump 100 and bolus reservoir 30 that avoids restrictor tubes 33, 34. In some embodiments, to further facilitate rapid priming, the bolus reservoir is provided in a deflated state prior to the first use of the infusion control device, minimizing the volume of air that must be expelled from the reservoir prior to filling. In some embodiments, rotation of the knob 51 to a position at which valves 31 and 32 are both opened has the further effect of causing the bolus reservoir to be deflated and held in a deflated state so that the fluid that flows through flow paths 36 and 37 does not accumulate in the bolus reservoir.

To deliver the basal rate of fluid flow, knob 51 is rotated to a position at which both valves 31 and 32 are closed. In this configuration, fluid flows only along basal flow path 35. The size of flow restrictor tube 33 is selected to achieve the desired basal flow rate.

To deliver a bolus dose, knob 51 is rotated to a "ready" position at which only valve 32 is opened. When the knob is depressed, the bottom of the knob exerts pressure on bolus reservoir 30, deflating the reservoir and ejecting the contents. The bolus dose flows via tubing sections 3034 and 3043 to output node 304 and is delivered to the patient 12.

Once a bolus dose has been delivered, knob 51 is rotated to close valve 32 and to allow delivery of fluid at the basal rate of flow to resume. Simultaneous to the fluid delivery along flow path 35, the bolus reservoir is being filled by fluid flowing along flow path 36; however, the delivery of a bolus dose during the filling period is blocked because valve 32 is closed. The bolus reservoir is prevented from being actuated again until a predetermined lock-out period has elapsed. The dimension of restrictor tube 34 controls the fill time of bolus reservoir 30 and thus establishes the length of the lock-out period.

Valves 31 and 32 are pinch tubes formed from a pliable material, such as silicone or polyvinyl chloride (PVC) of an appropriate durometric value. Nodes 301-304 are three port connectors made of PVC or another polymer that bonds easily with the tubing sections using commonly available solvents. Restrictor tubes 33 and 34 are, for instance, glass capillaries or PVC tubes of an appropriate inner lumen. Bolus reservoir 30 is a pliable chamber formed, e.g., of two welded PVC films. The bolus reservoir is designed to store a predetermined volume of fluid that can be discharged by actuating a mechanical force onto the films (for instance, by depressing knob 51, as discussed in greater detail below).

Figure 3:
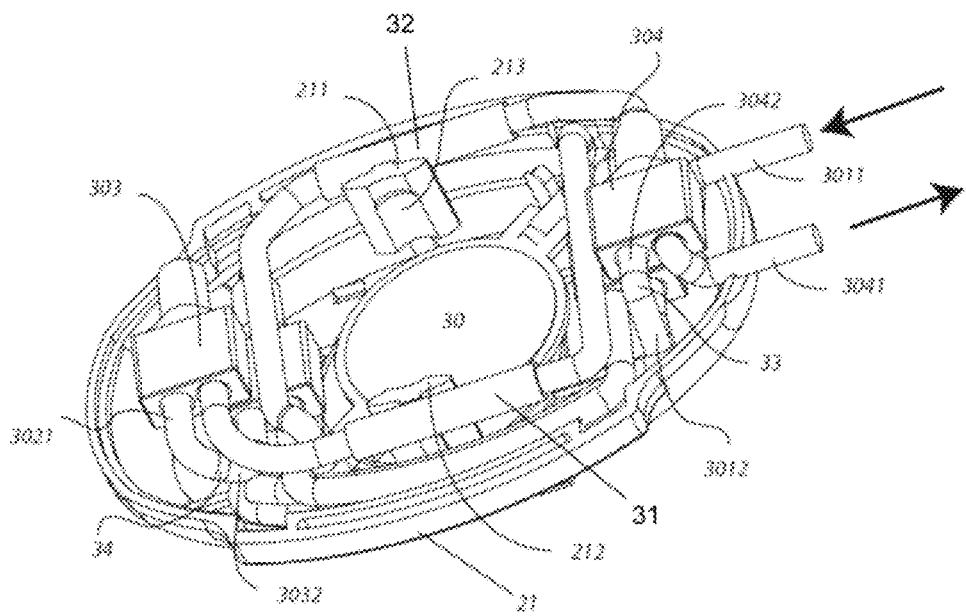
FIG. 3 is a schematic diagram of the internal structure of the infusion control device.
Figure 4:
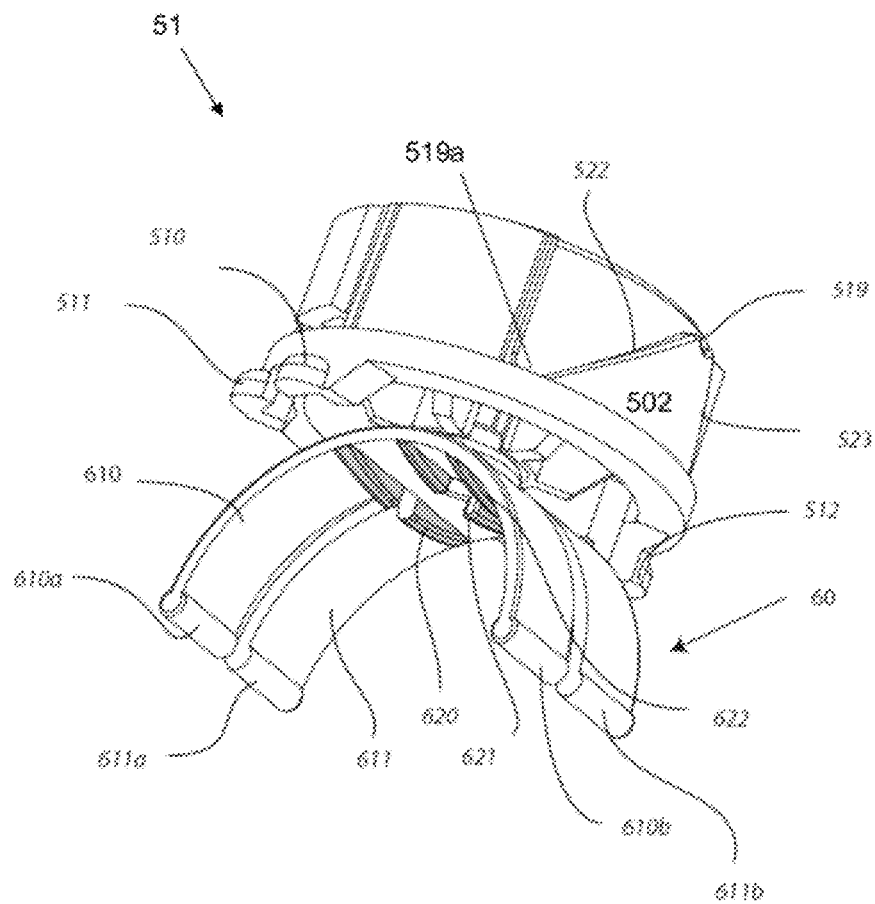
FIG. 4 is a schematic diagram of the structure of an actuator knob of an infusion control device.
Figure 5A:
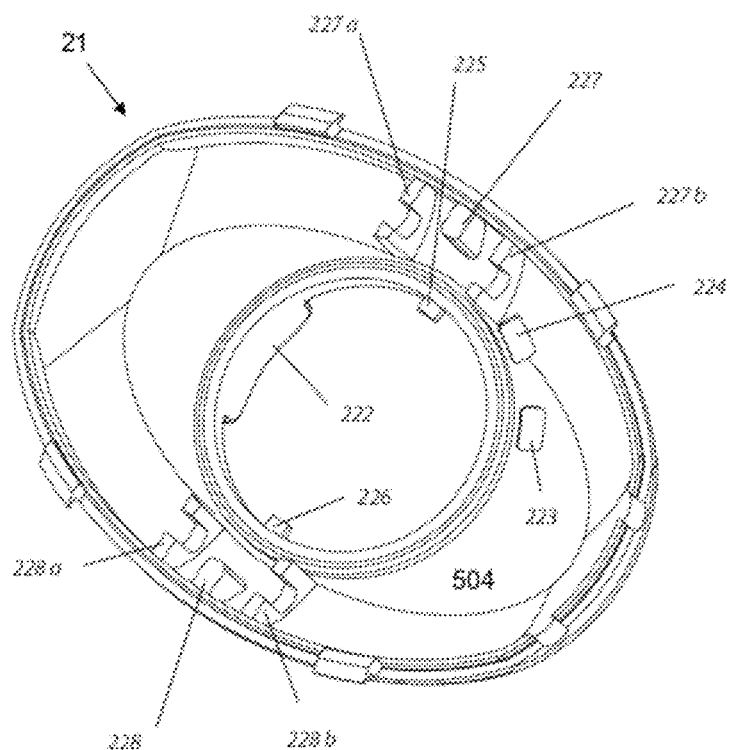
FIGS. 5A and 5B are schematic diagrams of the structure of the top housing of an infusion control device.

Referring to FIGS. 3, 4, and 5A, valves 31 and 32 are pinch tubes that are held in place on top housing 22 by holders 228a, 228b and 227a, 227b, respectively (FIG. 4A). Spherical protrusions 510, 511, 512 (FIG. 3) around the circumference of knob 51 work in conjunction with leaf springs 211 and 212 (FIG. 3) to open or close valves 32 and 31, respectively. To close one of the valves, knob 51 is rotated to a position at which one of the spherical protrusions 510, 511, or 512 is received by an indentation 213 or 214 on the leaf spring 211 or 212 corresponding to the desired valve. With the spherical protrusion held firmly in place by the indentation 213, 214, the valve 32 or 31, respectively, is pinched between the leaf spring 211 or 212 and a backstop 227 or 228 on top housing 22. The pinching is released (thus opening the valve) either when knob 51 is depressed such that the spherical protrusion is released from the indentation or when the knob is rotated such that the spherical protrusion is no longer aligned with the leaf spring. The leaf springs are arched and store an energy bias when pressed on by a spherical protrusion; when the force from the spherical protrusion is removed, the energy is released, causing the leaf spring to spring away from the pinch valve.

Referring now to FIGS. 1 and 4, knob 51 is affixed to a holder 70 (see FIG. 6A) atop an arched spring 60 and can rotate freely to allow selected of the desired mode of operation. Spring 60 exerts an upward force on knob 51. In the embodiment shown, spring 60 is formed of two strips 610, 611, allowing easy modification of the manufacturing tooling to accommodate parameters related to material properties, dimensions, and manufacturing processes. Spring 60 has rounded ends 610a, 611a and 610b, 611b such that they glide freely outward along rail-like guides (not shown) in bottom housing 22 when knob 51 is pushed downward, compressing the spring. That is, the guides ensure that the orientation of the spring ends is generally unchanged, thus maintaining the original alignment of spring 60 within the housing during knob depression or rotation. Spring 60 is molded of a material having sufficient elasticity, strength, and durability to allow both rotation and vertical movement of the knob 51. In some embodiments, a metal arched spring (not shown) is mounted next to spring 60 in order to provide additional desired physical attributes.

Spring 60 has three (or more, in some embodiments) rudder-like features 620, 621, 622 at the apex of its inner curved surface. The rudder-like features are spaced apart such that, when knob 51 is depressed, compressing spring 60, outside rudder-like features 620 and 622 move laterally away from the central rudder-like feature 621 (i.e., the arch between features 620 and 622 is slightly straightened). When knob 51 is sufficiently depressed, these rudder-like features come into contact with bolus reservoir 30, which is positioned below spring 60. The spreading movement of the rudder-like features creates a sweeping and squeezing effect which causes the contents of bolus reservoir 30 to be squeezed toward the edges of the reservoir and into the adjacent tubing.

Figure 5B:
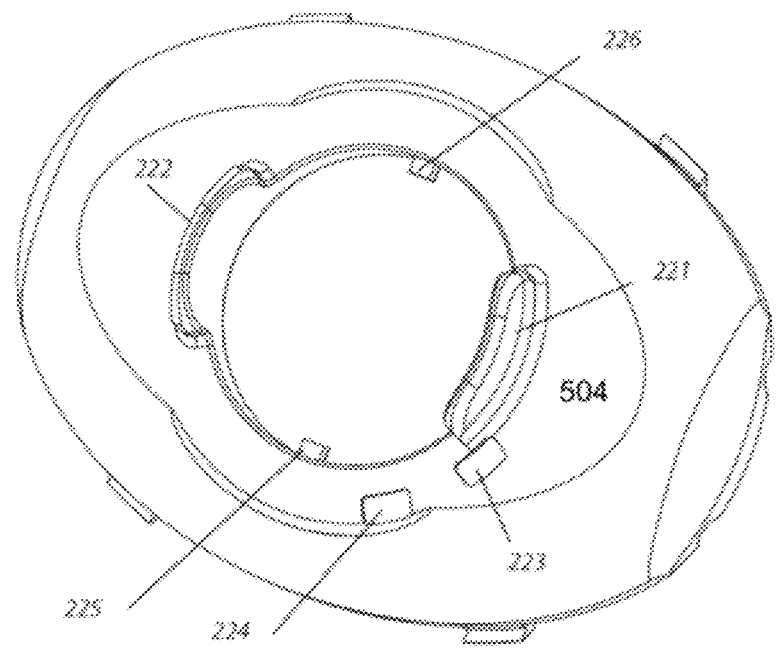

Referring also to FIGS. 5A and 5B, indentations 518, 519 are formed at the apex of corresponding triangular guides 500, 502, respectively, on knob 51. When knob 51 is pressed down and turned to the appropriate position, the indentations 518, 519 receive protrusions 225, 226, respectively, on an inner collar 504 of the upper housing 22, locking the knob in place. Gradient slopes 520, 521 on triangular guide 500 and gradient slopes 522, 523 on triangular guide 502 facilitate smooth rotation of the knob into and away from the position defined by the indentations 518, 519.

Figure 6A:
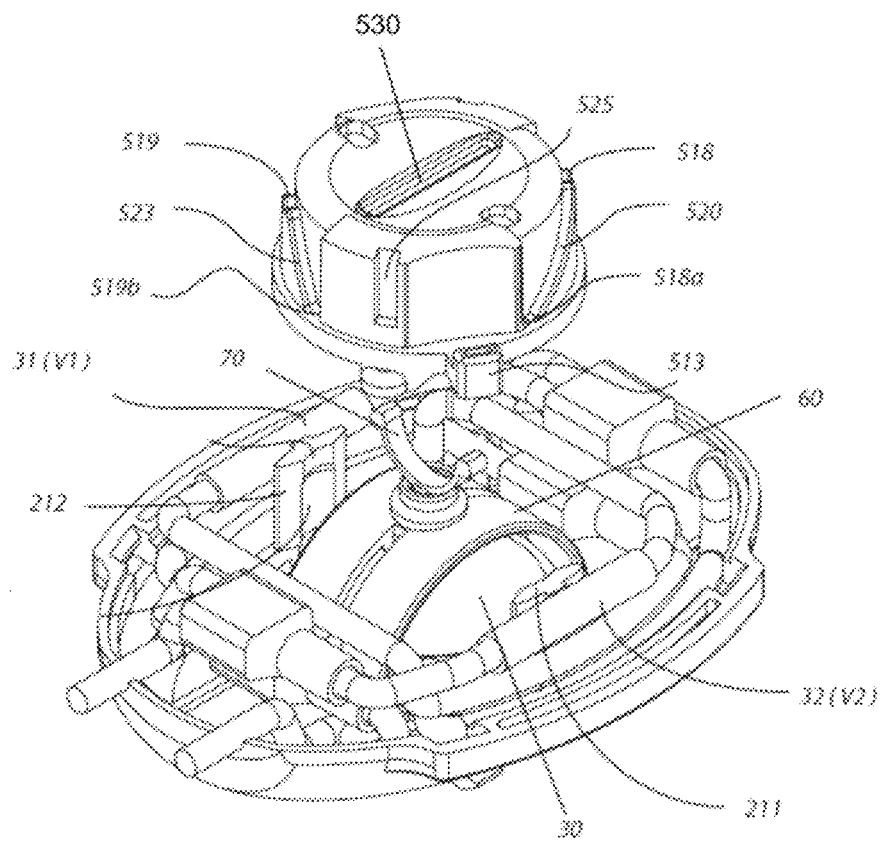
FIGS. 6A and 6B are schematic diagrams of an infusion control device set in quick prime mode.
Figure 6B:
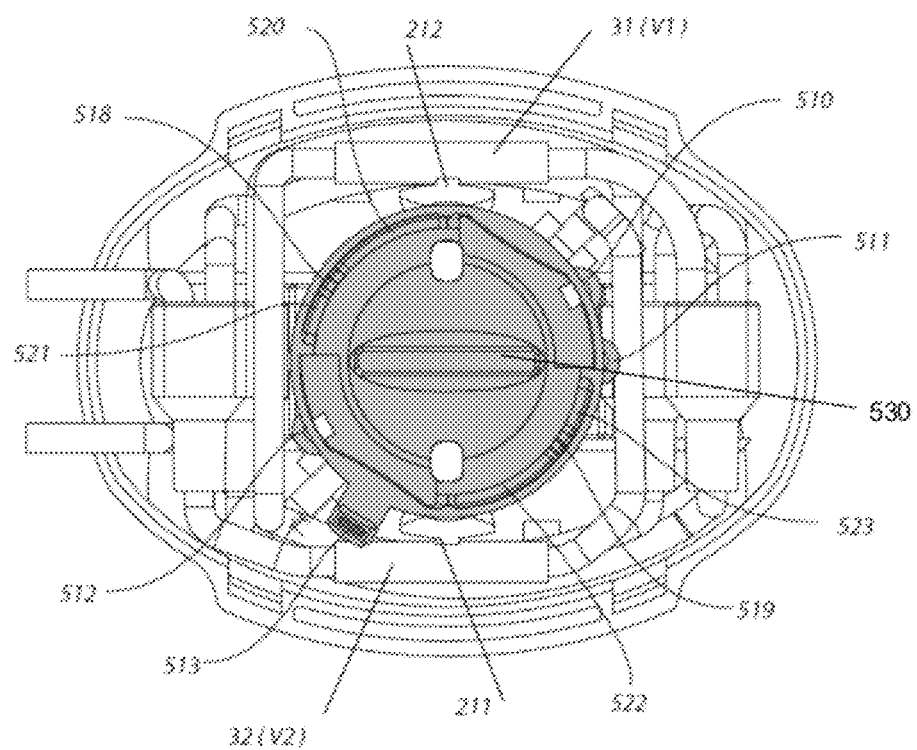

Referring to FIGS. 6A and 6B, in quick prime mode, knob 51 is depressed, with the protrusions 225, 226 on top housing 22 locked into the corresponding indentation 518, 519 on knob 51. Spring 60 is compressed by the lowered position of knob 51, and rudder-like features 620, 621, 622 are in contact with bolus reservoir 30. The bolus reservoir is generally deflated, presenting minimal air volume within its pliable chamber.

Valves 31 and 32 are open; that is, the leaf spring features 211 and 212 are not in contact with the spherical protrusions 510, 511, or 512 on knob 51. Because both valves are open, fluid communication between tubing sections 3022 and 3033 is allowed, as is fluid communication between tubing sections 3043 and 3034 (see FIG. 2A). More generally, all fluid pathways (35, 36, and 37) are open, allowing fluid communication between pump 100 and output tube 3041. As discussed above, opening valve 31 allows restrictor tube 34 to be bypassed, facilitating rapid priming and filling of the bolus reservoir.

In general, infusion control device 10 is generally presented in the quick prime configuration prior to its initial use.

Figure 7:
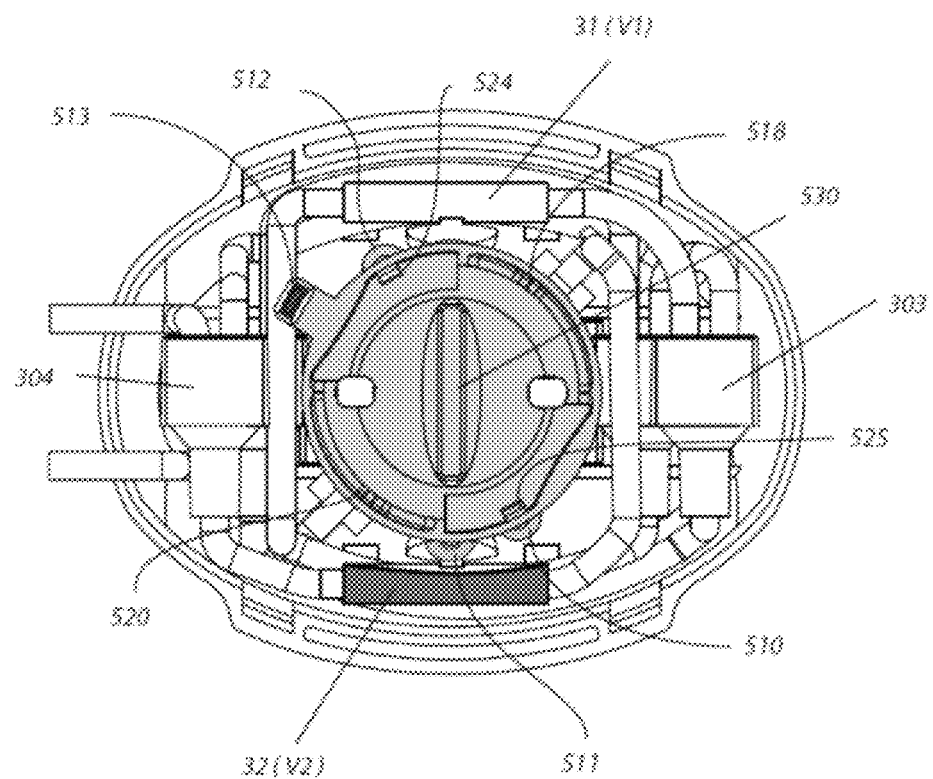
FIG. 7 is a schematic diagram of an infusion control device set in quick fill mode.

Referring to FIG. 7, in quick fill mode, knob 51 is not depressed and is rotated to a position at which the protrusions 225, 226 on top housing 22 are at the bottom of gradient slopes 522 or 523 and 532 or 533. To reach this position from the quick prime mode described above, knob 51 is rotated in a clockwise direction with the help of a slot 530. In some embodiments, output tube 3041 has a cap with chisel-shaped wings that can be inserted into slot 530 to facilitate turning the knob. A marker 513 on the circumferential edge of knob 51 appears in a window 223 (see FIG. 1) of top housing 22, indicating that the infusion control device is in quick fill mode.

In this configuration, the rudder-like features 620, 621, 622 under spring 60 are not in contact with bolus reservoir 30 until the reservoir is completely filled. Valve 31 is open, allowing fluid communication along second bolus flow path between nodes 302 and 303. The bolus reservoir is filled quickly because of the large dimension of valve 31 compared to restrictor tube 34. Valve 32 is closed by the alignment of spherical protrusion 511 with leaf spring 211, preventing outflow of fluid from the bolus reservoir during filling.

Figure 8A:
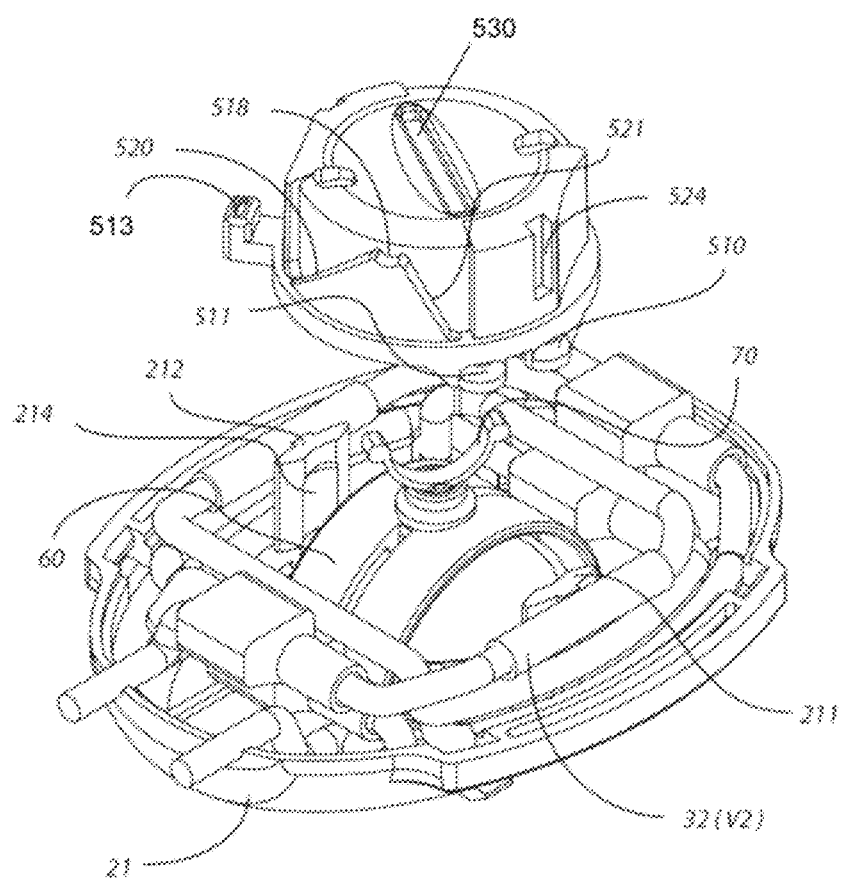
FIGS. 8A-8C are schematic diagrams of an infusion control device set in ready mode.
Figure 8B:
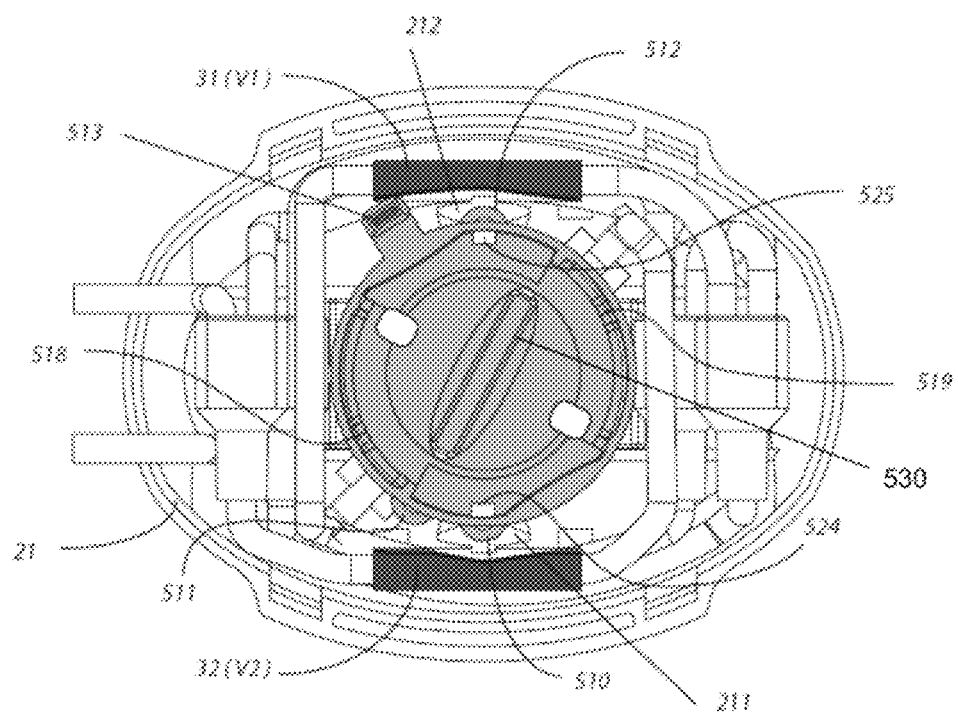
Figure 8C:
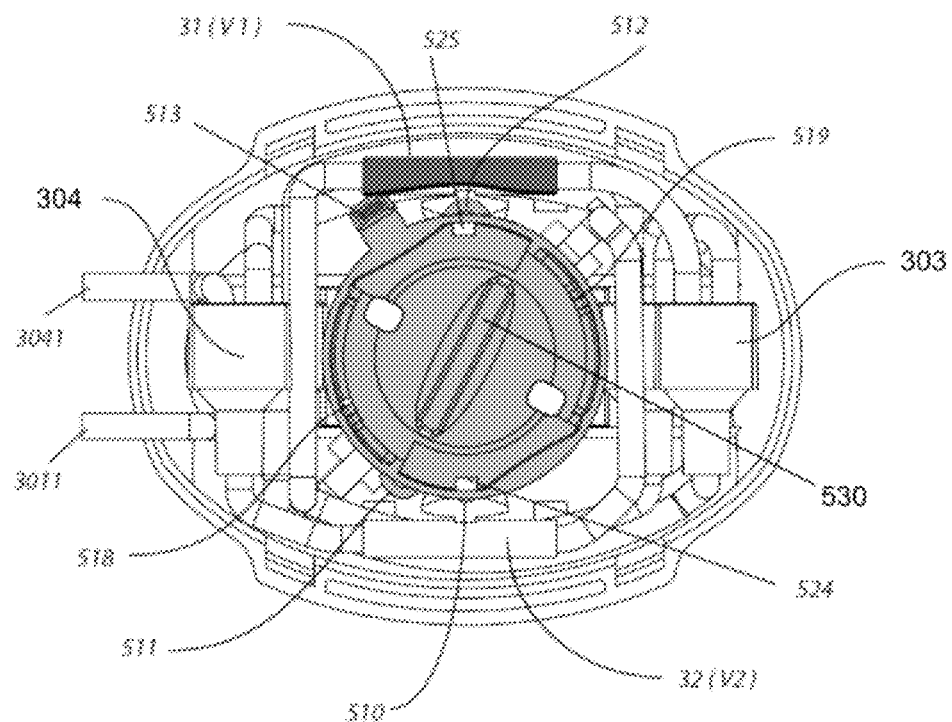

Referring to FIGS. 8A-8C, in ready (standby) mode, knob 51 is rotated to a position where both valves 31 and 32 are closed. Protrusions 225, 226 on top housing 22 are aligned in slots 525, 524 on the knob. Slots 524 and 525 are vertically oriented slots that function as guides when knob 51 is depressed. Marker 513 appears in a window 224 (see FIG. 1) of top housing 22, indicating that the infusion control device is in ready mode.

In the ready mode configuration, fluid can flow along basal flow path 35 via restrictor tube 33; that is, infusion control device 10 constantly delivers a basal flow rate. The bolus flow paths between nodes 302 and 304 are closed. When knob 51 is depressed, valve 32 opens, allowing fluid communication between bolus reservoir 30 and output node 304. The bolus reservoir is squeezed, as described above, and the bolus dose is delivered to patient 12. After actuation of knob 51 and administration of the bolus dose, the bolus reservoir 30 is refilled via first bolus flow path 36. The dimension of restrictor tube 34 is selected to achieve a predetermined time to fill bolus reservoir 30, preventing overdosage by frequent actuations of knob 51.

In some embodiments, basal flow path 35 is not provided such that infusion control device 10 delivers fluid only upon actuation of the bolus reservoir.

It is to be understood that the foregoing description is intended to illustrate and not to limit the scope of the invention, which is defined by the scope of the appended claims. Other embodiments are within the scope of the following claims.

What is claimed is:

1. A device for controlling delivery of a fluid from a fluid source to a patient, the device comprising:
   a first flow path between the fluid source and the patient, the first flow path for delivering the fluid from the fluid source to the patient at a basal rate of flow;
   a second flow path between the fluid source and the patient, the second flow path including:
      a first branch and a second branch;
      a bolus reservoir distal to the first branch and the second branch in the second flow path;
      a bolus valve disposed between the bolus reservoir and the patient;
      the first branch including a bolus restrictor tubing in which the fluid source is in fluid communication at a bolus filling rate with the bolus reservoir and the bolus valve; and
      the second branch including a branch valve in which the fluid source is in fluid communication with the branch valve, the bolus reservoir and the bolus valve; and
   a single actuator that actuates the bolus valve and the branch valve to operably select each of at least three modes of operation, the at least three modes of operation including a priming mode, a fill mode, and a standby mode:

the priming mode selected by the actuator opening the bolus valve and the branch valve such that the fluid flows through the first flow path, the first branch of the second flow path, and the second branch of the second flow path;

the fill mode selected by the actuator closing the bolus valve and opening the branch valve such that the fluid flows from the fluid source to the bolus reservoir via the second branch of the second flow path; and the standby mode selected by the actuator closing the bolus valve and the branch valve such that the fluid flows between the fluid source and the patient via the first flow path.

2. The device of claim 1, wherein, in the standby mode, the actuator is selectively further operable to open the bolus valve and apply a pressure to the bolus reservoir to cause the fluid stored in the bolus reservoir to flow to the patient.

3. The device of claim 1, wherein, in the standby mode, the actuator is selectively further operable to be depressed responsive to a user action.

4. The device of claim 1, wherein the first flow path includes a basal restrictor tube.

5. The device of claim 4, wherein the basal restrictor tube is dimensioned to allow a fluid flow through the first flow path at the basal rate of flow.

6. The device of claim 1, wherein the device is configured to allow filling of the bolus reservoir while the fluid is being delivered to the patient via the first flow path.

7. The device of claim 1, wherein the bolus filling rate is preselected based on a desired amount of time needed to fill the bolus reservoir with the fluid from the fluid source via the first branch of the second flow path.

8. The device of claim 1, wherein, in the standby mode, the fluid flows between the fluid source and the bolus reservoir via the first branch of the second flow path until the bolus reservoir is filled.

9. The device of claim 1, wherein the actuator is selectively rotatable to place the device in each of the at least three modes.

10. The device of claim 1, wherein the bolus valve and the branch valve are pinch tubes.

11. The device of claim 1, wherein the actuator is a knob operable by the patient.

12. The device of claim 1, wherein the fluid source is an infusion pump.

13. The device of claim 1, wherein the actuator is operable by the patient and restrains an ability of the patient to induce an overdose.

14. The device of claim 1, wherein after a bolus dose is delivered, the device provides for a lock-out period before a next bolus dose can be delivered.

15. A method for controlling delivery of a fluid from a fluid source to a patient using a device having a first flow path and a second flow path parallel to the first flow path, the method comprising:

providing the fluid at a basal rate of flow to the patient via the first flow path;

providing the fluid at a bolus filling rate of flow to a bolus reservoir via a bolus restrictor tube located within a first branch of the second flow path;

actuating a bolus valve and a branch valve with a single actuator to operably select each of at least three modes of operation, the at least three modes of operation including a priming mode, a fill mode, and a standby mode:

the priming mode selected by the actuator opening the bolus valve and the branch valve such that the fluid flows through the first flow path, the first branch of the second flow path, and a second branch of the second flow path;

the fill mode selected by the actuator closing the bolus valve and opening the branch valve such that the fluid flows from the fluid source to the bolus reservoir via the second branch of the second flow path;

the standby mode selected by the actuator closing the bolus valve and the branch valve such that the fluid flows between the fluid source and the patient via the first flow path; and in response to actuation of the bolus valve by the actuator, delivering a bolus dose of the fluid to the patient via the second flow path, the bolus dose being provided by opening with the actuator the bolus valve to release the bolus dose from the bolus reservoir, the bolus valve disposed along the second flow path.

16. The method of claim 15, wherein allowing the delivery of the fluid stored in the bolus reservoir includes opening the bolus valve disposed along the second flow path, wherein the bolus valve disposed along the second flow path is positioned between the bolus reservoir and the patient.

17. The method of claim 15, further comprising filling the bolus reservoir with the fluid from the fluid source while the fluid is being provided to the patient via the first flow path.

18. A device for controlling delivery of a fluid from a fluid source to a patient, the device comprising:

a first flow path between the fluid source and the patient, the first flow path for delivering the fluid from the fluid source to the patient at a basal rate of flow;

a second flow path between the fluid source and the patient, the second flow path including:
  a bolus reservoir;
  a bolus valve disposed between the bolus reservoir and the patient;
  a first branch including a bolus restrictor tubing in which the fluid source is in fluid communication at a bolus filling rate with the bolus reservoir and the bolus valve; and
  a second branch including a branch valve, and not including the bolus restrictor tubing, in which the fluid source is in fluid communication with the bolus reservoir and the bolus valve; and an actuator that is selectively rotatable to place the device in each of the following modes:
  a priming mode in which, when selected by the actuator, the actuator opens the bolus valve and the branch valve and the fluid flows through the first flow path, the first branch of the second flow path, and the second branch of the second flow path;
  a fill mode in which, when selected by the actuator, the actuator closes the bolus valve, opens the branch valve, and the fluid flows from the fluid source to the bolus reservoir via the second branch of the second flow path; and
  a standby mode in which, when selected by the actuator, the actuator closes the bolus valve and the branch valve and the fluid flows between the fluid source and the patient via the first flow path.

* * * * *